United States Patent [19]

Taft et al.

[11] Patent Number: 4,794,452
[45] Date of Patent: Dec. 27, 1988

[54] THROUGH FLAME OPTICAL VIEWING

[75] Inventors: Jeffrey D. Taft, Murrysville Boro; James F. Ellison, Pittsburgh, both of Pa.

[73] Assignee: Westinghouse Electric Corp., Pittsburgh, Pa.

[21] Appl. No.: 9,846

[22] Filed: Jan. 30, 1987

Related U.S. Application Data

[63] Continuation-in-part of Ser. No. 891,037, Jul. 31, 1986, abandoned.

[51] Int. Cl.$^4$ .............................................. H04N 7/18
[52] U.S. Cl. .................................... 358/100; 358/101; 358/107; 250/253; 350/311; 350/258
[58] Field of Search ............... 358/100, 101, 107, 113; 250/253, 330, 341; 350/311, 325.8

[56] References Cited

U.S. PATENT DOCUMENTS

| | | | |
|---|---|---|---|
| 3,718,758 | 2/1973 | Ponghis et al. | 358/100 |
| 4,084,188 | 0/1978 | Gorg et al. | 358/199 |
| 4,225,771 | 0/1980 | Justice et al. | 358/101 |
| 4,525,462 | 0/1985 | Behr | 501/71 |
| 4,539,588 | 0/1985 | Ariessohn et al. | 358/113 |

OTHER PUBLICATIONS

"Encyclopedia on Cathod-Ray Oscilloscopes and Their Uses", Rider et al., 1959 second edition, p. 4–4.

Primary Examiner—James J. Groody
Assistant Examiner—John K. Peng

[57] ABSTRACT

A method and apparatus for illuminating a target, for example the wall and internal structures of a coal, oil, or gas fired combustion chamber for remote viewing. A coherent light source is used to illuminate the target with illumination of a selected spectral content different from that produced by ambient light resulting from the combustion of the fuel. The coherent light illuminates the target and a narrow band optical filter is placed in front of a viewing camera to filter ambient light but to pass the illuminating source reflected from the target. The coherent light source has a wavelength range of about 422 nm to about 780 nm. Source wavelengths are chosen to be sufficiently long to penetrate particulate laden gases and still be distinguishable from thermal radiation inside the furnace. A human observer may manipulate the laser source and view the target using filter spectacles.

15 Claims, 1 Drawing Sheet

THROUGH FLAME OPTICAL VIEWING

CROSS REFERENCE TO A RELATED APPLICATION

This application is a continuation-in-part of U.S. application Ser. No. 891,037, filed July 31, 1986, now abandoned.

BACKGROUND OF THE INVENTION

1. Field of the Invention

This invention pertains generally to methods and apparatus employed to remotely view the walls and internal structures of combustion chambers. In particular, the invention relates to methods and apparatus for use in coal, gas, or oil fired furnaces.

2. Description of the Prior Art

A major difficulty exists in examining internal walls and internal structures of combustion chambers while in operation. Intense ambient light and heat from the combustion flames makes it difficult to make out structural and surface details due to the lack of contrast. In addition, the spectral content of the ambient light produced by the combustion flame usually contains certain dominant wavelengths which are largely determined by the type of fuel being used. When external sources of light are used to illuminate these structures and surfaces, it is difficult to discriminate the ambient light from the external source. This further complicates the problem of accurately observing details of the structures and surfaces to be studied.

The presence of intense light and heat is a particular problem when a human observer examines the combustion chamber through a viewing port, for example. Special equipment in the form of protective eye and or body wear in the obviously hostile environment makes it difficult to work and make observations for long periods of time. For example, protective eye wear attenuates the light over the entire visible spectrum and thus makes it difficult to observe details which are important.

Remote viewing is desirable because it removes the human observer from the hostile environment. However, equipment shortcomings sometimes make it difficult to obtain desired results using remote viewing techniques. For example, in the system of Ariessohn et al., U.S. Pat. No. 4,539,588, a remote viewing apparatus for a smelt bed includes a video camera fitted with an infrared (IR) imaging detector or vidicon tube to detect IR emission from the smelt bed. An objective lens obtains the image and an optical filter is interposed between the lens and the vidicon tube to selectively reject radiation less than about 1 micrometer to avoid fume interference. The filter is further selected to reject all but limited ranges of radiation; for example, the filter is centered about 1.68 micrometer with a bandwidth of about 0.07 micrometer. The problem with Ariessohn et al. is that no source of illumination other than the light within the flame is available to illuminate the smelt bed, and all ambient light except the long IR radiation is filtered out.

In Justice et al., U.S. Pat. No. 4,225,771, a high intensity monochromatic light source is projected toward a welding arc and welding puddle at a selected angle. A filter tuned to the wavelength of the monochromatic light source is placed in front of a remote viewing camera at the opposite side of the arc and at the selected angle. The light enhances the welding arc background while the filter attenuates the welding arc illumination that reaches the camera in order to enhance the contrast ratio between the welding arc, the weld puddle, and the surrounding area. Justice et al. is restricted to the particular angular viewing arrangement disclosed.

In Gourog et al., U.S. Pat. No. 4,084,188, an optical scanner is disclosed for scanning an object (e.g., a document) located in space. The object is exposed to ambient light. Relatively low intensity laser light is directed at the object through a beam splitter and a scanning deflector. Light scattered from the object is reflected back through the deflector and beam splitter to an optical sensor, including, a narrow band filter, a lens, and a photo detector. The laser light is modulated at a carrier frequency rate and the electrical signal from the photo detector is demodulated to produce a video signal. Ambient light is filtered by the narrow band filter. This system uses a most complex imaging technique for document reproduction, including light modulation which is not necessary in the subject invention.

Behr, U.S. Pat. No. 4,525,462, appears to disclose a furnace sight glass that filters infrared radiation.

None of the references appear to disclose any means for discriminating between visible wavelengths present in the ambient radiation and wavelengths of external sources of illumination.

Accordingly, an improved apparatus and method for viewing the internal structures and walls of a combustion chamber is desired that will enhance details of the wall surfaces and structures, and which is adapted for direct human viewing or remote viewing, and which is relatively simple to implement.

SUMMARY OF THE INVENTION

The invention is directed to a method and apparatus for viewing a combustion chamber in which ambient radiation is produced as a result of combustion of fuel. The ambient radiation contains particular dominant wavelengths which are fuel dependent. The system includes a coherent light source selected to generate light at a given intensity and wavelength, which wavelength is different from the fuel dependent dominant wavelengths. The coherent light source is focused to illuminate a target within the combustion chamber. Coherent light and ambient light reflected from the illuminated target are filtered at the source wavelength to thereby block most of the ambient light produced by the flame. The source wavelength is selected to be sufficiently long to penetrate particulate laden combustion gases and yet is sufficiently short to be distinguishable from thermal radiation emanating from the hot objects within the chamber. Viewing may be accomplished either locally or by means of a remote camera. Images from the camera may be processed in an image processing apparatus. The coherent light may be scanned over the target in raster fashion using a pair of galvanometer scanners synchronized to the sweep of the camera. The useful range of source wavelengths is between about 780 nm to about 422 nm.

BRIEF DESCRIPTION OF THE DRAWINGS

The invention may be better understood, and further advantages and uses thereof are readily apparent, when considered in view of the following detailed description of exemplary embodiments, taken with the accompanying drawings in which.

DESCRIPTION OF THE PREFERRED EMBODIMENTS

Figure 1:
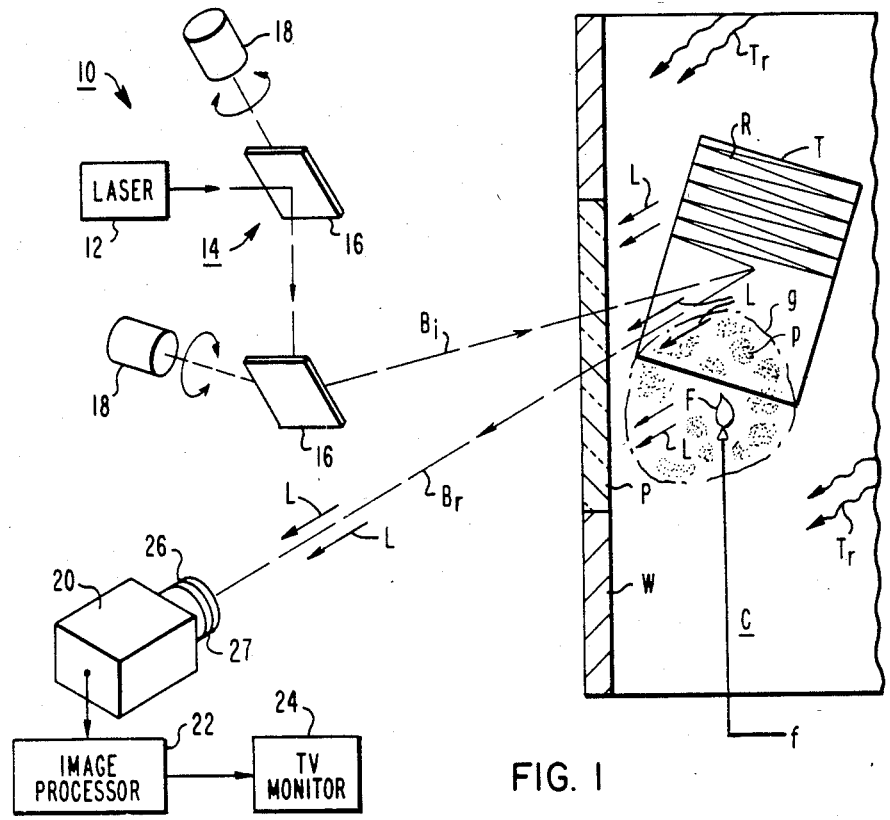
FIG. 1 is a schematic illustration of an embodiment of the present invention incorporating a remote viewing camera and a scanning deflector for the laser source of illumination.

The apparatus 10 of the present invention can be appreciated by reference to FIG. 1. A coherent source of illumination (source), such as a laser 12 (e.g. HeNe, HeCd, or laser diode) is adapted to illuminate a target T of interest in a combustion chamber C. Relevant portions of the combustion chamber are illustrated schematically as a wall W having a viewing port P therein. Remaining portions of the combustion chamber C are fragmented. Port P may be open or formed of glass as shown. The laser 12 produces an incident beam $B_i$ which is carried to the target T through a deflector 14 including a pair of mirrors 16, each driven by associated scanning galvanometers 18. The deflector 14 scans the target T in a raster scan pattern R as shown. A solid state camera, such as a charge coupled device (CCD) video camera 20 views the target T. The scan of the camera 20 and raster are synchronized. The incident beam $B_i$ is scattered by the target T. A portion of the scattered or reflected radiation (reflected beam $B_r$) is received by the camera 20. In the embodiment shown, the output of the camera 20 is coupled to an image processor 22 and a TV monitor 24.

Ambient light L is produced by flame F as a result of combustion of fuel f. The combustion process may also produce gas g laden with particles p. Ambient light L reaches the camera 20 either directly or by scattering from the target T. The camera 20 has a narrow band optical filter 26 tuned to the wavelength of laser 12. The filter 26 may be located over camera lens 27 or in the path of the reflected beam $B_r$. Filter 26 selectively rejects all but the laser wavelengths including substantially all of the ambient light L.

The spectral content of the ambient light L is largely determined by the composition of the fuel being burned. For example, a natural gas flame produces ambient light L dominated by wavelengths near the shorter or blue end of the visible spectrum. Thus, the laser 12 should not produce light $B_i$ dominated by the same wavelengths. Otherwise, it will be difficult, if not impossible, to distinguish light $B_i$ from the laser 12 and ambient light L. Accordingly, the laser 12 should operate closer to the red end of the spectrum, for example, a laser diode operating at 780 nm or a HeNe laser operating at 633 nm.

Propane fuel with sodium contamination produces a more yellow flame F than the flame produced by natural gas. An HeNe laser operating at about 633 nm is a source which may be readily distinguished from such a flame. Acetylene and coal fired flames have spectra dominated wavelengths longer than natural gas and propane. Thus, sources with spectra dominant in the blue are preferred. For example, an HeCd laser operating at about 422 nm is effective. Incoherent, high intensity white light produced by a quartz halogen lamp in combination with a low pass filter has been shown to work but with high energy costs and low resolution.

Oil is believed to produce a flame similar in spectral content to coal and acetylene. Thus, an HeCd laser operating at 422 nm is thought to be an effective illumination source.

In addition to the difficulties associated with distinguishing spectrally similar sources of radiation discussed above, particles p in combustion gases g tend to scatter much of the light within the combustion chamber C, including the ambient light L and the incident and reflected laser light $B_i$ and $B_r$. Thus, in particulate laden flames, the laser 12 should be tuned to a wavelength which, in addition to avoiding spectral interference, should be long enough to penetrate the particulate laden gases g in the combustion chamber C and short enough to be distinguishable from long wavelengths associated with thermal radiation $T_r$ emanating from hot objects with the combustion chamber C. It has been found that lasers operating at wavelengths in the range of about 633 nm to about 780 nm are useful.

The incident beam $B_i$ thus penetrates the particulate laden gas within the combustion chamber C and strikes the target T in the raster pattern R. Scattered or reflected radiation $B_r$ from the target T is detected by the camera 20. Ambient light L and thermal radiation $T_r$ are filtered by the narrow band pass optical filter 26 which rejects substantially all but a narrow range of wavelengths centered about the laser 12 wavelength.

The present invention contemplates that a human observer (not shown) wearing a pair of goggles or face plate fitted with the narrow band optical filter 26 centered at the wavelength of the laser 12 may visually observe the target area. In a sense, the laser 12 may be used as a high intensity flashlight to illuminate specific points in the target T. The laser 12 may be hand manipulated.

Figure 2:
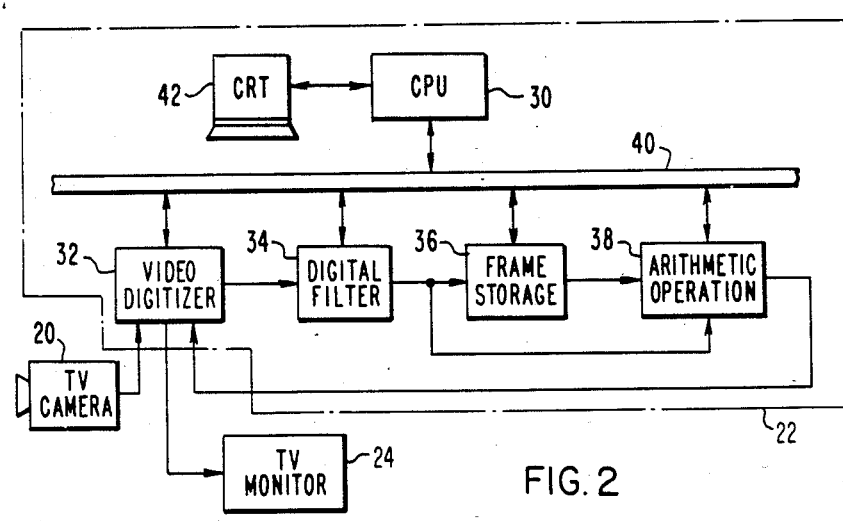
FIG. 2 is a schematic illustration of an image enhancing circuit.

FIG. 2 illustrates an exemplary image processor 22 or image enhancer useful in implementing the present invention. The image processor 22 includes a mini computer or CPU 30, a video signal digitizer 32, a two dimensional linear digital filter 34, a frame storage device 36, and an arithmetic operator 38.

The TV camera 20 produces a known RS-170 video signal which is coupled to the digitizer 32 and constructed into a digital stream of data. The digital filter 34 has a three by three coefficient window and performs a finite impulse response (non-recursive) filtering at TV frame rates. Frame storage device 36 can hold two complete frames of video data. The arithmetic unit 38 responsive to frame storage device 36 and filter 34 accepts the digital video signal data streams and applies arithmetical logical operation to combine them into a single output stream on a pixel by pixel basis. The output of arithmetic operation is coupled to digitizer 32 for conversion into a TV image for monitor 24. The CPU 30 is coupled to the outputs of each of the digitizer 32, filter 34, frame storage 36 and arithmetic operation unit 38 by means of a bus 40. A CRT 42 coupled to the CPU 30 may be used for real time observation as well as word and data manipulation.

The image processor 22 performs high pass filtering for edge enhancement, low pass filtering for pixel based time domain averaging or smoothing, delayed frame pixel multiplication to remove transient effects, and histogram modification and pseudocolor. The monitor 24 is coupled to the digitizer and may be used for real time observation. The image processor preferably includes commercially available equipment as set forth below:

Video digitizer 32—Datacube DIGIMAX;

Linear digital filter 34—Datacube VFIR including three by three coefficient window;

Frame storage 36—Datacube FRAME STORE;

Arithmetic unit 38 Operation—Datacube MAX-SP; and

CPU 30—MIZAR 7100 CPU including M68001 processor, 512K bytes ram, 2 serial ports and real time clock; and Bus—VME.

There has thus been provided a method and apparatus employing the concepts of the present invention which allow visual and remote inspection of heated surfaces and structures within the hostile environment of a combustion chamber and the like.

We claim as our invention:

1. A viewing system external to a combustion chamber for viewing internal surfaces therein in which intense ambient light is produced in said combustion chamber comprising: a coherent light source external to the combustion chamber operable to generate visible illuminating light of a given intensity and at a wavelength distinguishable from the ambient light substantially within a preselected visible wavelength band between about 422 and 780 nm, which coherent light source is operable when directed to illuminate a target within the combustion chamber with said visible illuminating light; and means external to the combustion chamber for viewing the illuminated portion of the target including means for filtering said ambient light produced in the combustion chamber including ambient light reflected from the target to pass the wavelength of the illuminating light through the viewing means and rejecting the ambient light produced within the combustion chamber.

2. A method of viewing a target within a furnace which is illuminated by visible ambient light as a result of combustion of fuel comprising the step of: illuminating a portion of the target with coherent visible illuminating light of a given intensity and at a wavelength distinguishable from the ambient light substantially within a preselected wavelength band between about 422 and 780 nm, filtering the light reflected from the target to be viewed to pass the wavelength of the illuminating light.

3. An apparatus for optically scanning a target with relatively long wavelength visible radiation, which target is simultaneously exposed to relatively high intensity visible ambient radiation to produce a video signal substantially unaffected by the ambient radiation comprising: a laser light source for producing a visible illuminating light having a wavelength between about 422 and 780 nm, which wavelength is distinguishable from the ambient radiation, a beam deflector including optical means directing the light from the source through said beam deflector to the target to be scanned, a narrow band optical filter constructed and positioned to pass light having the wavelength of said source, which light is reflected from the scanned target, and a video camera positioned to receive light passed by the optical filter operative to produce an electrical video signal representing the scanned target.

4. An apparatus for optically scanning a target exposed to visible ambient light to produce a signal substantially unaffected by the ambient light comprising: a laser source for producing a beam of visible illuminating light of a given wavelength between about 422 and 780 nm distinguishable from the ambient light, a beam deflector including optical means directing light from said laser source through said beam deflector to the target to be scanned, a narrow band optical filter constructed and positioned to pass the illuminating light at the wavelength of said laser source which is reflected from the scanned target, and a video camera positioned to receive the light passed by the optical filter to produce a video signal representing the scanned target.

5. An apparatus for illuminating a target exposed to high intensity visible ambient radiation which masks the target comprising: a laser source for producing a beam of coherent visible light at a selected wavelength between about 422 and 780 nm and distinguishable from the ambient radiation, means directing the laser beam towards the target, and a narrow band optical filter constructed and positioned to pass light therethrough having the wavelength of the laser source which is reflected from the target, which narrow band optical filter is positionable in front of a human viewer and which laser source is manipulable by the viewer.

6. An apparatus for viewing for a target in a combustion chamber being subjected to relatively high intensity ambient radiation in the visible and infrared spectrum, which ambient radiation is produced by the combustion of fossil fuels containing particulate laden combustion gases, comprising a laser for producing a visible beam of coherent light, distinguishable from the ambient radiation, and of a relatively long wavelength between about 422 and 780 nm sufficient to penetrate the particulate laden combustion gases and impinge on the target, means for viewing reflected radiation from the target and a filter tuned to the wavelength of the laser and located between the target and the viewing means for filtering the ambient radiation to distinguish the laser radiation reflected from the target.

7. A viewing system for viewing internal surfaces in a combustion chamber, said surfaces illuminated by ambient light resulting from combustion of fuel therein and having a given spectral content dependent upon the type of fuel used, which spectral content is dominated by particular wavelengths, said viewing system comprising: a visible coherent illuminating light source external to the combustion chamber operable to generate light of a selected wavelength substantially within a preselected wavelength band between about 422 and 780 nm different than and distinguishable from the dominant wavelengths in the ambient light, which coherent light source is operable when directed to illuminate a selected target within the combustion chamber; and means for viewing the portion of the target including means centered at the selected wavelength of the illuminating light source for filtering light reflected from the target to pass only the reflected illuminating light from the internal surfaces to the viewing means and rejecting other sources of radiation.

8. The viewing system of claim 7 wherein the coherent light source is produced by a laser.

9. A method of viewing a target illuminated by ambient light resulting from combustion of fuel, said ambient light having a spectral content determined by the fuel combusted in the chamber, said spectral content being dominated by certain wavelengths, said target being located in a heated combustion chamber, said method comprising the steps of: illuminating a portion of the target with a source of visible coherent light of a selected wavelength substantially within a preselected bandwidth between about 422 or 780 nm different than and distinguishable from the dominant wavelengths of the ambient light, generating the illumination external to the combustion chamber, narrowly filtering the light reflected from the target to be viewed to pass only the wavelength of the source.

10. A viewing apparatus comprising: means for optically scanning a target with a coherent source of visible illuminating radiation of a selected wavelength, said target being simultaneously exposed to relatively high intensity ambient radiation of a relatively broad bandwidth dominated by selected wavelengths, and wherein the source has a spectral content substantially different than and distinguishable from the ambient radiation between about 422 and 780 nm, said viewing apparatus producing a video signal substantially unaffected by the ambient radiation including, a beam deflector including optical means for directing the illuminating radiation from the source through said beam deflector to the target to be scanned, a narrow band optical filter constructed and positioned to pass radiation reflected from the scanned target having a wavelength centered at the wavelength of said source, and a video camera positioned to receive said radiation passed by the optical filter and being operative to produce an electrical video signal representing the scanned target.

11. The apparatus of claim 10 wherein a video camera is a charge coupled device.

12. The apparatus of claim 10 wherein the laser beam source is one of an HeNe and laser, an HeCd laser and a laser diode source.

13. An apparatus for optically scanning a target exposed to ambient light of a given spectral content to produce a signal substantially unaffected by the ambient light comprising: a laser source for producing a visible light beam of a given wavelength and spectral content different than and distinguishable from the ambient light, a beam deflector including optical means directing light from said laser source through said beam deflector to the target to be scanned, a narrow band optical filter for passing light at the wavelength of said source which is reflected from the target, and a video camera positioned to receive light passed by the optical filter to produce a video signal representing the scanned target.

14. An apparatus for illuminating a target exposed to high intensity ambient radiation of a given spectral content in the visible spectrum comprising: a laser beam source for producing a visible illuminating laser beam having a spectral content different than and distinguishable from the ambient light, means directing the laser beam from the source to the target and a narrow band optical filter for passing light having the wavelength of the source which is reflected from the target, which narrow band optical filter is positionable in front of a human viewer and which laser source may is manipulable by the viewer.

15. An apparatus for viewing comprising: laser means for producing a beam of visible radiation of a given wavelength for illuminating a target in a combustion chamber, said target being subjected to relatively high intensity ambient radiation of a given fuel dependent spectral content in the visible and infrared which radiation is produced by the combustion of fossil fuels, combustion products of which fuels contain particulate matter, said laser means for producing said beam of radiation having spectral wavelength content different than and distinguishable from the ambient radiation and of a relatively long wavelength sufficient to penetrate the particulate laden combustion gases and impinge on a target, means for viewing radiation reflected from the target, and a narrow band filter, tuned to the wavelength of the laser means, located between the target and the viewing means for allowing the reflected laser radiation to pass therethrough for filtering the ambient radiation produced in the combustion chamber to thereby distinguish the laser radiation reflected from the target.

* * * * *